(12) United States Patent
Lord et al.

(10) Patent No.: US 11,020,550 B2
(45) Date of Patent: Jun. 1, 2021

(54) DEVICE AND SYSTEM

(71) Applicant: Nerudia Limited, Liverpool (GB)

(72) Inventors: Chris Lord, Liverpool (GB); David Jones, Liverpool (GB); Kenneth Scott, Liverpool (GB); Stephen McDonald, Liverpool (GB); Thomas Sudlow, Liverpool (GB)

(73) Assignee: NERUDIA LIMITED, Liverpool (GB)

( * ) Notice: Subject to any disclaimer, the term of this patent is extended or adjusted under 35 U.S.C. 154(b) by 249 days.

(21) Appl. No.: 16/328,198

(22) PCT Filed: Aug. 25, 2017

(86) PCT No.: PCT/GB2017/052509
§ 371 (c)(1),
(2) Date: Feb. 25, 2019

(87) PCT Pub. No.: WO2018/037245
PCT Pub. Date: Mar. 1, 2018

(65) Prior Publication Data
US 2019/0231998 A1    Aug. 1, 2019

(30) Foreign Application Priority Data

Aug. 25, 2016  (GB) .................................. 1614518

(51) Int. Cl.
*A61M 15/06* (2006.01)
*A24F 47/00* (2020.01)
(Continued)

(52) U.S. Cl.
CPC ........... *A61M 15/06* (2013.01); *A24F 47/008* (2013.01); *A61M 11/042* (2014.02);
(Continued)

(58) Field of Classification Search
CPC ... A61M 15/06; A61M 1/042; A61M 15/0021
(Continued)

(56) References Cited

U.S. PATENT DOCUMENTS

| 5,388,594 A | 2/1995 | Counts et al. |
| 6,098,632 A | 8/2000 | Turner et al. |

(Continued)

FOREIGN PATENT DOCUMENTS

| KR | 2020100002737 | 3/2010 |
| WO | 2015/101479 | 7/2015 |

(Continued)

OTHER PUBLICATIONS

PCT International Search Report for PCT/GB2017/052509 dated Oct. 27, 2017; pp. 1-4.

*Primary Examiner* — Neil Abrams
(74) *Attorney, Agent, or Firm* — Brandon V. Zuniga; James R. Gourley; Carstens & Cahoon, LLP

(57) ABSTRACT

There is disclosed a device for nicotine delivery, comprising: a vapour outlet conduit for coupling to, and for fluid communication with, a vapour creation system, said vapour outlet conduit defining a fluid passage therethrough for delivery of vapour from a vapour creation system to a user; wherein said vapour outlet conduit comprises a nicotine carrier unit region configured to accept a nicotine carrier unit and retain said nicotine carrier unit in said fluid passage. Also disclosed is a system for nicotine delivery and kits-of-parts for assembling the device and system.

17 Claims, 8 Drawing Sheets

(51) Int. Cl.
*A61M 11/04* (2006.01)
*A61M 15/00* (2006.01)

(52) U.S. Cl.
CPC .... *A61M 15/0021* (2014.02); *A61M 15/0035* (2014.02); *A61M 15/0041* (2014.02); *A61M 2205/3653* (2013.01); *A61M 2205/8206* (2013.01)

(58) Field of Classification Search
USPC ........................................................ 131/329
See application file for complete search history.

(56) References Cited

U.S. PATENT DOCUMENTS

| | | | |
|---|---|---|---|
| 10,076,140 B2* | 9/2018 | Silvestrini | H05B 1/0244 |
| 10,085,482 B2* | 10/2018 | Silvestrini | A24B 15/16 |
| 10,645,973 B2* | 5/2020 | Silvestrini | H05B 6/108 |
| 2011/0226236 A1 | 9/2011 | Buchberger | |
| 2012/0247494 A1 | 10/2012 | Oglesby et al. | |
| 2015/0040930 A1 | 2/2015 | Robinson et al. | |
| 2015/0351456 A1 | 12/2015 | Johnson et al. | |
| 2016/0029699 A1 | 2/2016 | Li et al. | |
| 2016/0135506 A1 | 5/2016 | Sanchez et al. | |
| 2019/0231998 A1* | 8/2019 | Lord | A61M 15/0035 |

FOREIGN PATENT DOCUMENTS

| | | |
|---|---|---|
| WO | 2015/179002 | 11/2015 |
| WO | 2015/197627 | 12/2015 |
| WO | 2015/197863 | 12/2015 |
| WO | 2016/075747 | 5/2016 |

* cited by examiner

DEVICE AND SYSTEM

CROSS-REFERENCE TO RELATED APPLICATIONS

This application is a US 371 Application from PCT/GB2017/052509 Aug. 25, 2017, which claims priority to GB Application 1614518.7 filed Aug. 25, 2016, the technical disclosures of which are hereby incorporated herein by reference.

TECHNICAL FIELD

The present invention relates to a device and system for nicotine delivery and particularly, but not exclusively, to a device and system where release of nicotine from a nicotine-bearing carrier may be achieved without direct heating of the nicotine-bearing carrier.

BACKGROUND

Nicotine delivery devices and systems fall into two broad categories: a first, non-powered category and a second, powered category.

Devices or systems in the first category may comprise nicotine replacement therapy devices such as "inhalators", e.g. Nicorette® Inhalator. Inhalators generally allow nicotine to be inhaled through an elongate tube in which a container containing a nicotine carrier is located. An air stream caused by suction through the tube by the user carries nicotine vapours or an aerosolised mist of nicotine to the user to satisfy a nicotine craving. The container may comprise a replaceable cartridge, which includes a cartridge housing and a passageway in the housing in which a nicotine reservoir is located. The reservoir holds a measured amount of nicotine in the form of the nicotine carrier. The measured amount of nicotine is an amount suitable for delivering a specific number of "doses". The form of the nicotine carrier is such as to allow nicotine to be atomised or aerosolised into a fluid stream passing around or through the reservoir. Thus, when a user "sucks" or inhales through the device, nicotine is atomised or aerosolised from the reservoir and is absorbed through the mucus membranes in the mouth and throat, rather than travelling into the lungs. The passageway generally has an opening at each end for communication with the exterior of the housing and for allowing the fluid stream through the passageway. A nicotine-impermeable barrier seals the reservoir from atmosphere. The barrier includes passageway barrier portions for sealing the passageway on both sides of the reservoir. These barrier portions are frangible so as to be penetrable for opening the passageway to atmosphere.

Devices or systems in the second category may comprise electronic devices or systems that permit a user to simulate the act of smoking by producing an aerosol mist or vapour that is drawn into the lungs through the mouth and then exhaled. The inhaled aerosol mist or vapour typically bears nicotine and/or other flavourings without the odour and health risks associated with traditional smoking and tobacco products. In use, the user experiences a similar satisfaction and physical sensation to those experienced from a traditional smoking or tobacco product, and exhales an aerosol mist or vapour of similar appearance to the smoke exhaled when using such traditional smoking or tobacco products.

Nicotine delivery devices or systems of the second category generally use heat and/or ultrasonic agitation to vaporize a solution comprising nicotine and/or other flavouring, propylene glycol and/or glycerine-based base into an aerosol mist of vapour for inhalation.

A person of ordinary skill in the art will appreciate that nicotine delivery devices or systems of the second, powered category as used herein include, but are not limited to, electronic nicotine delivery systems, electronic cigarettes, e-cigarettes, e-cigs, vaping cigarettes, pipes, cigars, cigarillos, vaporizers and devices of a similar nature that function to produce an aerosol mist or vapour that is inhaled by a user. Such nicotine delivery devices or systems of the second category incorporate a liquid reservoir element generally including a vaporizer or misting element such as a heating element or other suitable element, and are known inter alia, as atomizers, cartomizers, or clearomizers. Some electronic cigarettes are disposable; others are reusable, with replaceable and refillable parts.

Nicotine delivery devices or systems falling into the second category may typically resemble a traditional cigarette and are generally cylindrical in form with a mouthpiece at one end through which the user can draw the aerosol mist or vapour for inhalation. These devices or systems usually share several common components: a power source such as a battery, a reservoir for holding the liquid to be vaporized, a vaporization component for atomizing and/or vaporizing the liquid and to thereby produce an aerosol mist and/or vapour, and control circuitry operable to actuate the vaporization component responsive to an actuation signal from a switch operative by a user or upon detection of air being drawn through the mouthpiece, i.e. when the user sucks or inhales.

The reservoir of nicotine delivery devices or systems of the second category may be either a replaceable or refillable container that is coupled to, or located in, the main body of the nicotine delivery device and that is typically made of a resilient plastic material such as high-density polypropylene. The reservoir generally contains a wicking material in which the liquid is stored but may just be a storage space without any wicking material. Once the replaceable or refillable reservoir is emptied it must either be replaced or refilled.

Replaceable type reservoirs are typically provided in the form of a pre-filled cartridge that can be securely and removably engaged to, or within, the cylindrical main body of the nicotine delivery device. These reservoir and vaporization elements may also be integrated into a single component commonly known as a "cartomizer" that may be disposable or refillable.

The ingredients of the liquid for producing the aerosol mist or vapour in nicotine delivery devices or systems of the second category vary widely, but typically include water and flavourings in a propylene glycol and/or glycerol base. Nicotine may also be included in solutions intended to fulfil a nicotine replacement role, without the harmful products associated with tobacco smoke.

A person of ordinary skill in the art will appreciate that the term "liquid" as used herein, may include, but is not limited to, any liquids, gels, powders and gases together with liquids comprising mixtures of liquids, gels, powders and gases that are capable of being atomized or vaporized whether or not using heat and/or ultrasonics.

Nicotine delivery devices or systems falling within the second category may be preferable to some users because of the user experience that devices in this category provide, i.e. a perceived similar satisfaction and perceived similar physical sensations to those experienced from using a traditional smoking or tobacco product. These similarities may be perceived due to the user inhaling a warm vapour (due to heating processes within the devices), which may mimic the so-called "throat-hit" that is experienced when using traditional smoking or tobacco products. "Throat-hit" is generally used to describe the physical sensation of inhaled smoke from traditional smoking or tobacco products passing through the throat.

However, a potential drawback associated with nicotine delivery devices or systems falling within the second category may arise due to the nicotine carrier and vapour precursor (i.e. ingredients for producing an aerosol mist or vapour) being combined within a liquid. Heating of the liquid to vaporise the vapour precursor (i.e. to create the aerosol mist or vapour) also heats the nicotine carrier. If the nicotine carrier is heated by too great an amount, then this can effectively boil the nicotine carrier and may cause unpleasant flavours to be released in the aerosol mist or vapour. This can detract from the user experience.

A further potential drawback may arise due to the liquid undergoing repeated heating and cooling cycles. Repeated heating and cooling of the liquid may change the ratio, within the liquid, of nicotine carrier to vapour precursor (i.e. ingredients for producing the aerosol mist or vapour) within the liquid. This may result in a change in an amount of nicotine delivered (i.e. nicotine dose per inhalation) over time.

A yet further drawback may arise in instances when a user wishes to change from using a liquid with nicotine to a nicotine-free liquid. Where a liquid reservoir of the device contains a liquid containing nicotine and the user wishes to change to a nicotine-free liquid, this will require draining and cleaning of the reservoir prior to re-filling with nicotine-free liquid to avoid contamination. Alternatively, the user may remove the liquid reservoir from the device and replace it with a reservoir containing nicotine-free liquid. Both of these processes may be time-consuming and inconvenient for the user.

Aspects and embodiments of the invention were devised with the foregoing in mind.

BRIEF SUMMARY OF THE PRESENT INVENTION

According to an aspect of the present invention, there is provided a device for nicotine delivery, comprising: a vapour outlet conduit for coupling to, and for fluid communication with, a vapour creation system, the vapour outlet conduit defining a fluid passage therethrough for delivery of vapour from a vapour creation system to a user; wherein the vapour outlet conduit comprises a nicotine carrier unit region configured to accept a nicotine carrier unit and retain the nicotine carrier unit in the fluid passage.

In the device above, the region for holding a nicotine carrier unit is separate from a vapour creation system. The separation of the nicotine carrier unit from the system where heating occurs, i.e. the vapour creation system, may result in no direct heating of nicotine, nicotine compounds, nicotine precursor materials, etc. in the device. This may mitigate the problems described above.

Optionally, the vapour outlet conduit may be: releasably coupleable to the vapour creation system, e.g. to permit location of the nicotine carrier unit in the vapour outlet conduit; and/or separable to permit location of the nicotine carrier unit therein.

Optionally, the device may further comprise a nicotine carrier unit located in the fluid passage, the nicotine carrier unit configured for removable location within the fluid passage and comprising a nicotine-bearing substrate configured for entraining nicotine in a vapour stream received from the vapour creation system as the vapour stream passes through the vapour outlet conduit.

Providing nicotine in the device by way of a separate nicotine carrier unit may allow a user to reconfigure a nicotine carrying device to a nicotine-free device by removal of a nicotine carrier unit from the vapour outlet conduit. Similarly, a nicotine-free device could be reconfigured as a nicotine carrying device by inserting a nicotine carrier unit in the vapour outlet conduit.

Optionally, the nicotine carrier unit may be configured, and located within the vapour outlet conduit, for passage of the vapour stream over and/or through the nicotine-bearing substrate.

The nicotine-bearing substrate may comprise a porous material where pores of the porous material hold, contain, carry, or bear at least one of: nicotine; a nicotine precursor; and a nicotine compound. Optionally, the porous material may comprise a sintered material such as, for example, BioVyon™ (by Porvair Filtration Group Ltd). Further optionally, the nicotine-bearing substrate may comprise polypropylene or polyethylene terephthalate.

The nicotine carrier unit may be configured as a housing for housing the nicotine-bearing substrate and, optionally, the housing may define a passageway in which is located the nicotine-bearing substrate. Further optionally, the housing may comprise penetrable seals for closing open ends of the passageway, the penetrable seals penetrable to permit fluid communication through the passageway. Yet further optionally, the vapour outlet conduit comprises penetrating elements for penetrating the penetrable seals of the housing.

Optionally, the vapour outlet conduit may be disposable and/or replaceable.

Optionally, the vapour outlet conduit may comprise a mouthpiece of the nicotine delivery device.

According to another aspect of the present invention, there is provided a nicotine carrier unit for a device as described above or hereinafter, wherein the nicotine carrier unit is configured for removable location within the fluid passage and comprising a nicotine-bearing substrate configured for releasing nicotine to a vapour stream as the vapour stream passes through the vapour outlet conduit.

According to a further aspect of the present invention, there is provided a system for nicotine delivery, comprising: a nicotine delivery device as described above or hereinafter, and a vapour creation system coupled to the vapour outlet conduit of the nicotine delivery device.

According to another aspect of the present invention, there is provided a kit-of-parts for assembling a device for nicotine delivery comprising: a vapour outlet conduit configured for coupling to, and for fluid communication with, a vapour creation system, the vapour outlet conduit defining a fluid passage therethrough for delivery of vapour from a vapour creation system to a user, wherein the vapour outlet conduit comprises a nicotine carrier unit region configured to accept a nicotine carrier unit and retain the nicotine carrier unit in the fluid passage; and a nicotine carrier unit configured for removable location in the fluid passage, the nicotine carrier unit comprising a nicotine-bearing substrate configured for releasing nicotine to a vapour stream as the vapour stream passes through the vapour outlet conduit.

According to another aspect of the present invention, there is provided a kit-of-parts for assembling a system for nicotine delivery, comprising: a vapour outlet conduit configured for coupling to, and for fluid communication with, a vapour creation system, the vapour outlet conduit defining a fluid passage therethrough for delivery of vapour from a vapour creation system to a user, wherein the vapour outlet conduit comprises a nicotine carrier unit region configured to accept a nicotine carrier unit and retain the nicotine carrier unit in the fluid passage; a nicotine carrier unit configured for removable location in the fluid passage, the nicotine carrier unit comprising a nicotine-bearing substrate configured for releasing nicotine to a vapour stream as the vapour stream passes through the vapour outlet conduit; and a vapour creation system for coupling to vapour outlet conduit.

BRIEF DESCRIPTION OF THE DRAWINGS

One or more embodiments in accordance with aspects of the present invention will be described, by way of example only, and with reference to the following drawings in which.

DETAILED DESCRIPTION OF THE INVENTION

In general outline, one or more embodiments in accordance with the present invention provide a device for nicotine delivery in which a nicotine-bearing substrate may be inserted into a fluid passage of the device. The fluid passage is configured to direct air and/or vapour and/or an aerosolised mist past, through and/or in proximity to, the nicotine-bearing substrate. In one or more embodiments, a vapour or mist creation system is coupled to the device to form a system for nicotine delivery.

Hereinafter, and for convenience only, "device for nicotine delivery" shall be referred to as "nicotine delivery device" and "system for nicotine delivery" shall be referred to as "nicotine delivery system".

Figure 1:
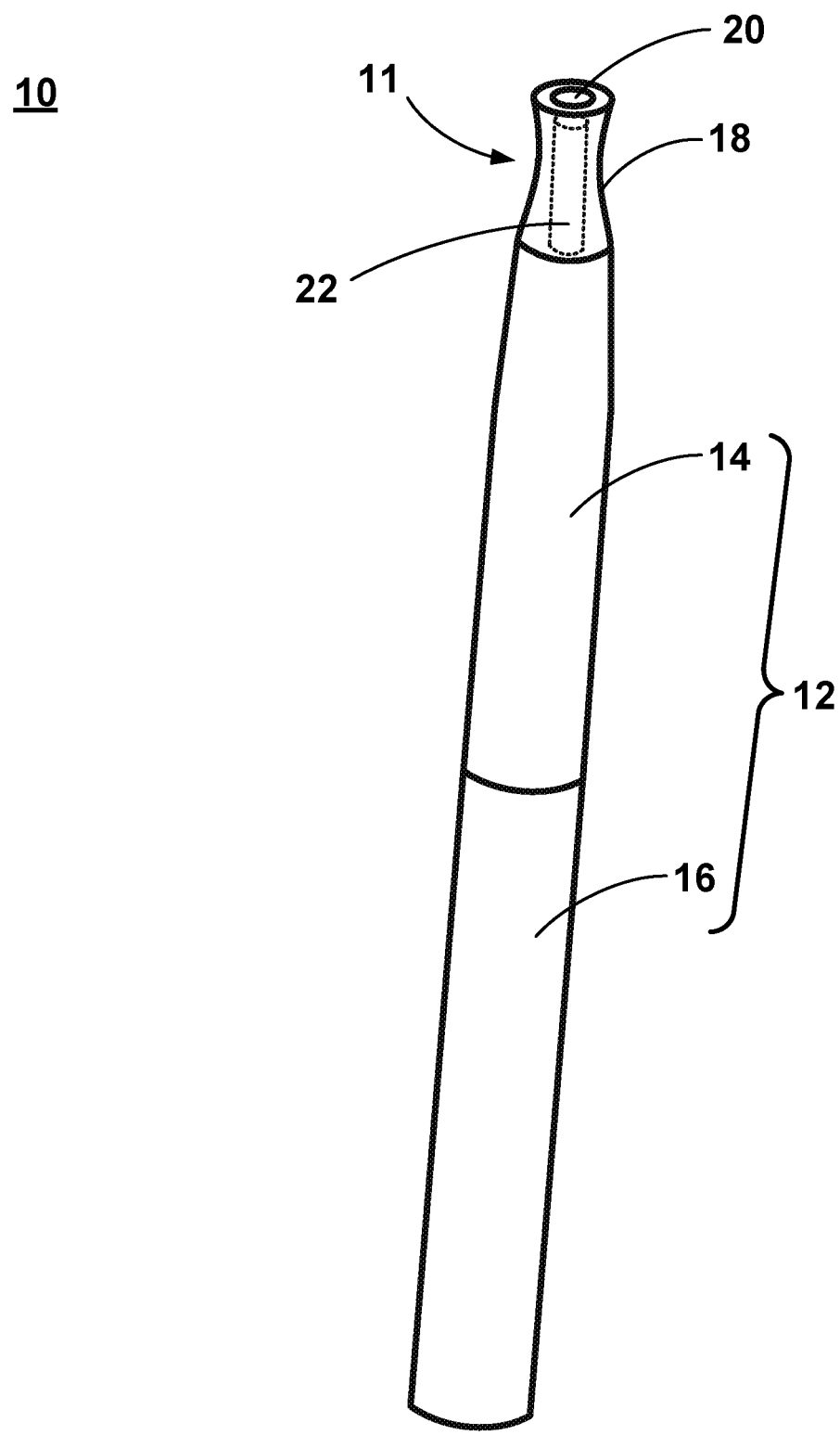
FIG. 1 is a perspective view illustration of a system and device for nicotine delivery according to one or more embodiments of the present invention.

Referring now to FIG. 1, there is a perspective view of a nicotine delivery system 10 such as, for example, an e-cigarette device, comprising a nicotine delivery device 11 and a vapour or aerosolised mist creation system 12. Hereinafter, and for convenience only, "vapour or aerosolised mist creation system 12" shall be referred to as "vapour creation system 12".

The nicotine delivery device 11 comprises a vapour or mist outlet conduit 18 coupled to, and in fluid communication with, the vapour creation system 12. Hereinafter, and for convenience only, "vapour or mist outlet conduit 18" shall be referred to as "vapour outlet conduit 18".

The vapour outlet conduit 18 comprises a tubular element, through which is provided a fluid passage 20 for delivery of vapour or aerosolised mist from the vapour creation system 12 to a user. The vapour outlet conduit 18 is configured for insertion into the user's mouth so that vapour or aerosolised mist produced by the nicotine delivery system 10 can be delivered to the user when the user sucks or inhales.

A carrier unit 22 (e.g. a capsule) is located in the fluid passage 20 of the vapour outlet conduit 18. The carrier unit 22 contains at least one of: nicotine; a nicotine precursor material; and a nicotine compound, and is configured to allow air and/or vapour or aerosolised mist passing through the fluid passage 20 to flow therethrough. As vapour or aerosolised mist from the vapour creation system 12 passes through the carrier unit 22, nicotine may be entrained in the air and/or vapour or aerosolised mist stream from a substrate bearing the nicotine, nicotine precursor material and/or nicotine compound, e.g. via diffusion.

The carrier unit 22 is removable from the fluid passage 20 so that it may be disposed of when expired. After removal of a used carrier unit 22 a replacement carrier unit 22 can be inserted into the fluid passage 20 to replace the used carrier unit 22. The vapour creation system 12 comprises a vaporizer portion 14 and a battery portion 16 mechanically and electrically coupled to the vaporizer portion 14.

The vaporizer portion 14 may also be known inter alia, as an atomizer, cartomizer, or clearomizer, and may comprise any suitable device for heating liquid to create a vapour or mist.

Responsive to activation of the vapour creation system 12, vapour or aerosolised mist produced by the vapour creation system 12 passes into an "upstream" region of the fluid passage 20 of vapour outlet conduit 18. The vapour or aerosolised mist continues through the carrier unit 22 and nicotine from the nicotine precursor material and/or nicotine compound in carrier unit 22 becomes entrained in the vapour or aerosolised mist stream. The vapour or aerosolised mist stream containing nicotine passes from the carrier unit 22 into a "downstream" region of the fluid passage 20 before exiting the fluid passage 20.

For the avoidance of doubt, the term "upstream" defines a position towards the point at which a fluid will be drawn into the vapour outlet conduit 18 when it is in use, i.e. a point from which air and/or vapour or aerosolised mist is drawn into the vapour outlet conduit 18 from atmosphere and/or from the vapour creation system 12. The term "downstream" defines a position from the point at which fluid containing nicotine exits the carrier unit 22. Based on these definitions, any fluid in the fluid passage 20 that is "upstream" of the carrier unit 22 does not contain nicotine and any fluid in the fluid passage that is "downstream" of the carrier unit 22 may contain nicotine (dependent upon whether or not the carrier unit 22 contains nicotine precursor material and/or a nicotine compound and the extent to which nicotine is drawn into the fluid as it traverses the carrier unit 22).

Figure 2:
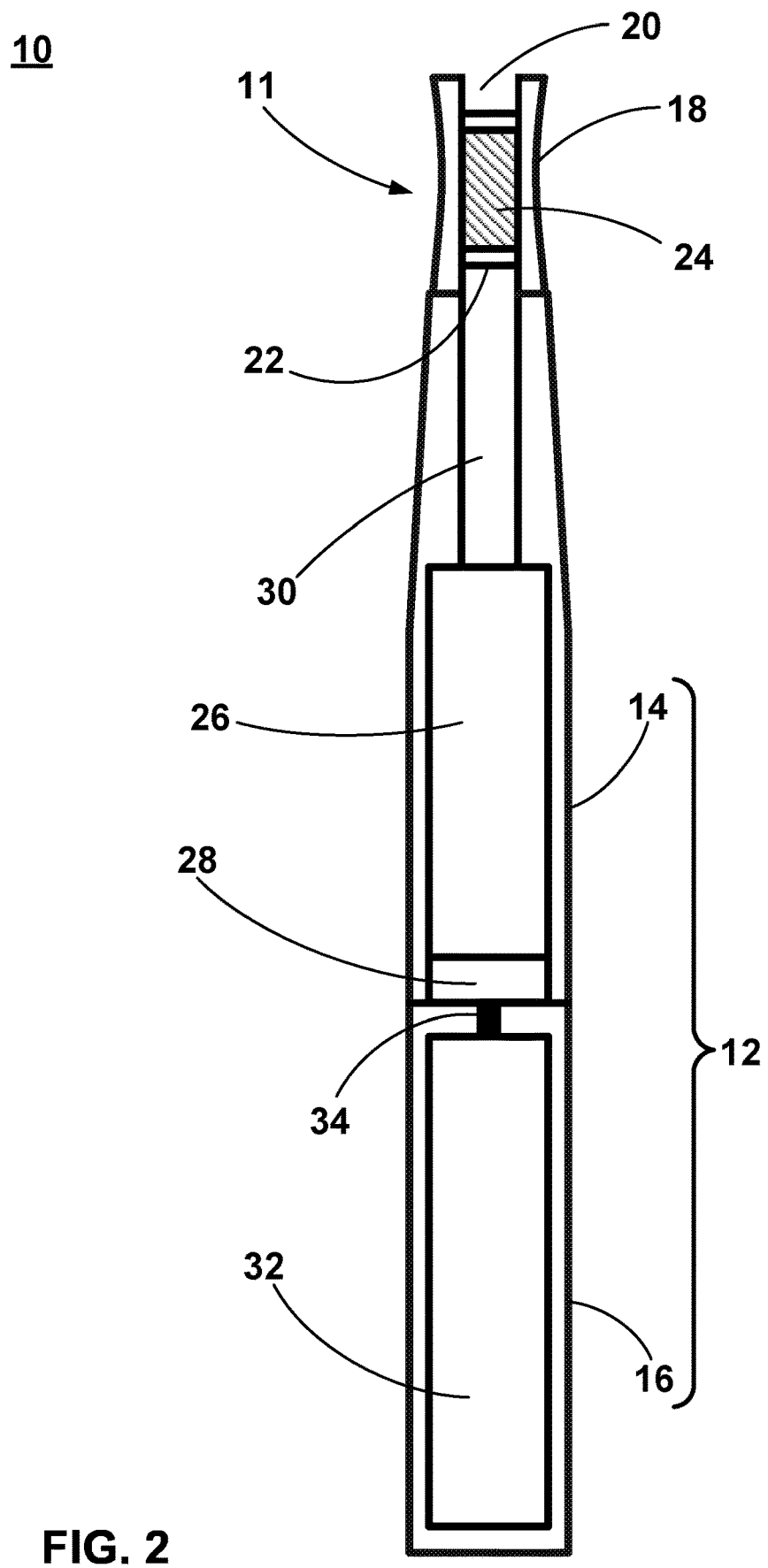
FIG. 2 is a cross-sectional side view illustration of the system and device for nicotine delivery of FIG. 1.

Turning now to FIG. 2, a cross-sectional side view of the nicotine delivery system 10 is schematically illustrated showing the features described above in relation to FIG. 1 in more detail.

As can be seen in FIG. 2, the carrier unit 22 contains a substrate 24, which, in one or more embodiments, is impregnated with nicotine precursor material and/or a nicotine compound. Optionally, the substrate 24 may comprise a porous material where pores of the porous material hold the nicotine precursor material and/or the nicotine compound. Further optionally, the porous material may comprise a sintered polymer such as, for example, BioVyon™ (by Porvair Filtration Group Ltd). The porous material of substrate 24 is configured for "wicking" or "drawing" nicotine precursor material away from end regions of the substrate 24 (i.e. toward a centre region of the substrate 24). This may prevent leakage of nicotine precursor material from the substrate (and thus from the carrier unit 22 when penetrable films (not shown in FIG. 2—see FIG. 4) sealing the carrier unit are broken). Thus, nicotine precursor material may be held within the substrate 24 until airflow therethrough (i.e. during use) causes atomisation of nicotine from the nicotine precursor material.

Vaporizer portion 14 of vapour creation system 12 comprises a reservoir 26 configured to contain ingredients for producing an aerosol mist or vapour, a vaporizing or misting arrangement 28 configured to vaporize or aerosolise the ingredients for producing an aerosol mist or vapour and a fluid passage 30 for delivery of vapour or aerosolised mist formed from the ingredients for producing an aerosol mist or vapour to the fluid passage 20 of the vapour outlet conduit 18. Hereinafter, and for convenience only, "vaporizing or misting arrangement 28" shall be referred to as "vaporizing arrangement 28".

The ingredients for producing an aerosol mist or vapour may be in liquid form and may comprise one or more of glycol, polyglycol, propylene glycol and water.

The vaporizing arrangement 28 comprises a chamber (not shown) for holding ingredients for producing an aerosol mist or vapour received from the reservoir 26 and a heating element (not shown) for heating ingredients for producing an aerosol mist or vapour in the chamber.

The vaporizing arrangement 28 further comprises a conduit (not shown) in fluid communication with the chamber and configured to deliver vapour or mist formed from heated ingredients for producing an aerosol mist or vapour in the chamber to the fluid passage 30.

The vaporizing arrangement 28 further comprises control circuitry (not shown) operative by a user, or upon detection of air and/or vapour or aerosolised mist being drawn though the vapour outlet conduit 18, i.e. when the user sucks or inhales.

Battery portion 16 of the vapour creation system 12 comprises a battery 32 and a coupling 34 for mechanically and electrically coupling the battery portion 16 to the vaporizer portion 14. When the battery portion 16 and vaporizer portion 14 are coupled as shown in FIG. 2, battery 32 is electrically coupled to the vaporizing arrangement 28 to supply power thereto.

Responsive to activation of the control circuitry of vaporizing arrangement 28, the heating element heats the ingredients for producing an aerosol mist or vapour in the chamber of the vaporizing arrangement 28. Vapour or aerosolised mist formed as a result of the heating process passes through the conduit into the fluid passage 30 of the vaporizer portion 14. This vapour or aerosolised mist then passes into an upstream region of fluid passage 20 of the vapour outlet conduit 18, through the carrier unit 22, where nicotine from the substrate 24 becomes entrained in the fluid stream, and then onwards through the downstream region of fluid passage 20 for delivery to the user.

Figure 3:
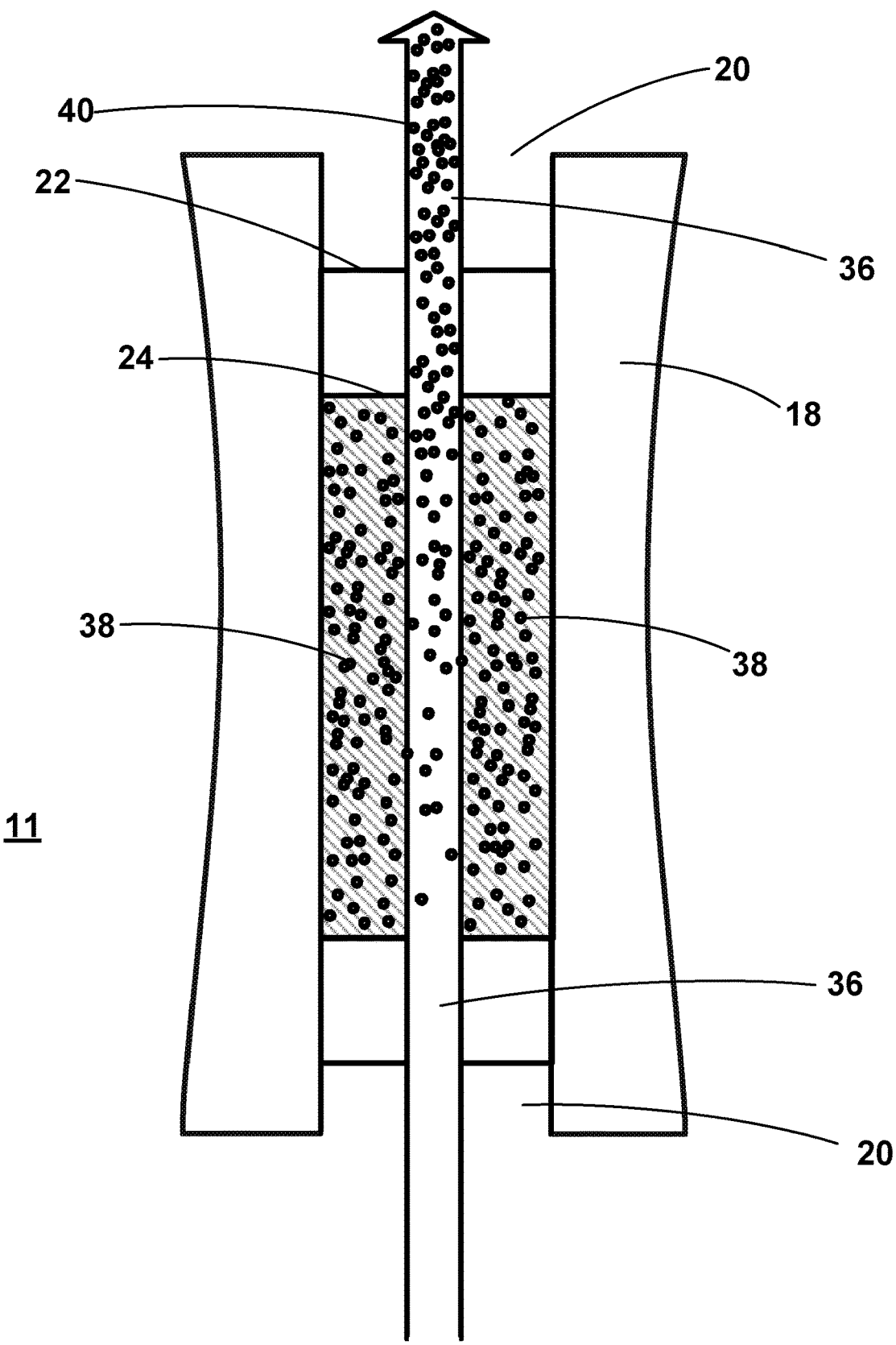
FIG. 3 is a cross-sectional side view illustration of a vapour outlet conduit of the system and device for nicotine delivery of FIGS. 1 and 2 according to one or more embodiments of the present invention.

This process is illustrated in FIG. 3, where arrow 36 schematically denotes the flow of the fluid stream from the fluid passage of the vaporizer portion to the upstream region of fluid passage 20 of the vapour outlet conduit 18, through the carrier unit 22, and then through the downstream region of fluid passage 20 for delivery to the user.

FIG. 3 also schematically illustrates nicotine and/or nicotine compounds 38 contained in the substrate 24 and the nicotine and/or nicotine compounds passing from the substrate 24 into the fluid stream 36 (e.g. a stream containing vapour or aerosolised mist), i.e. becoming entrained in the fluid stream 36. Nicotine and/or nicotine compounds within the fluid stream 36 are denoted by reference numeral 40.

Figure 4:
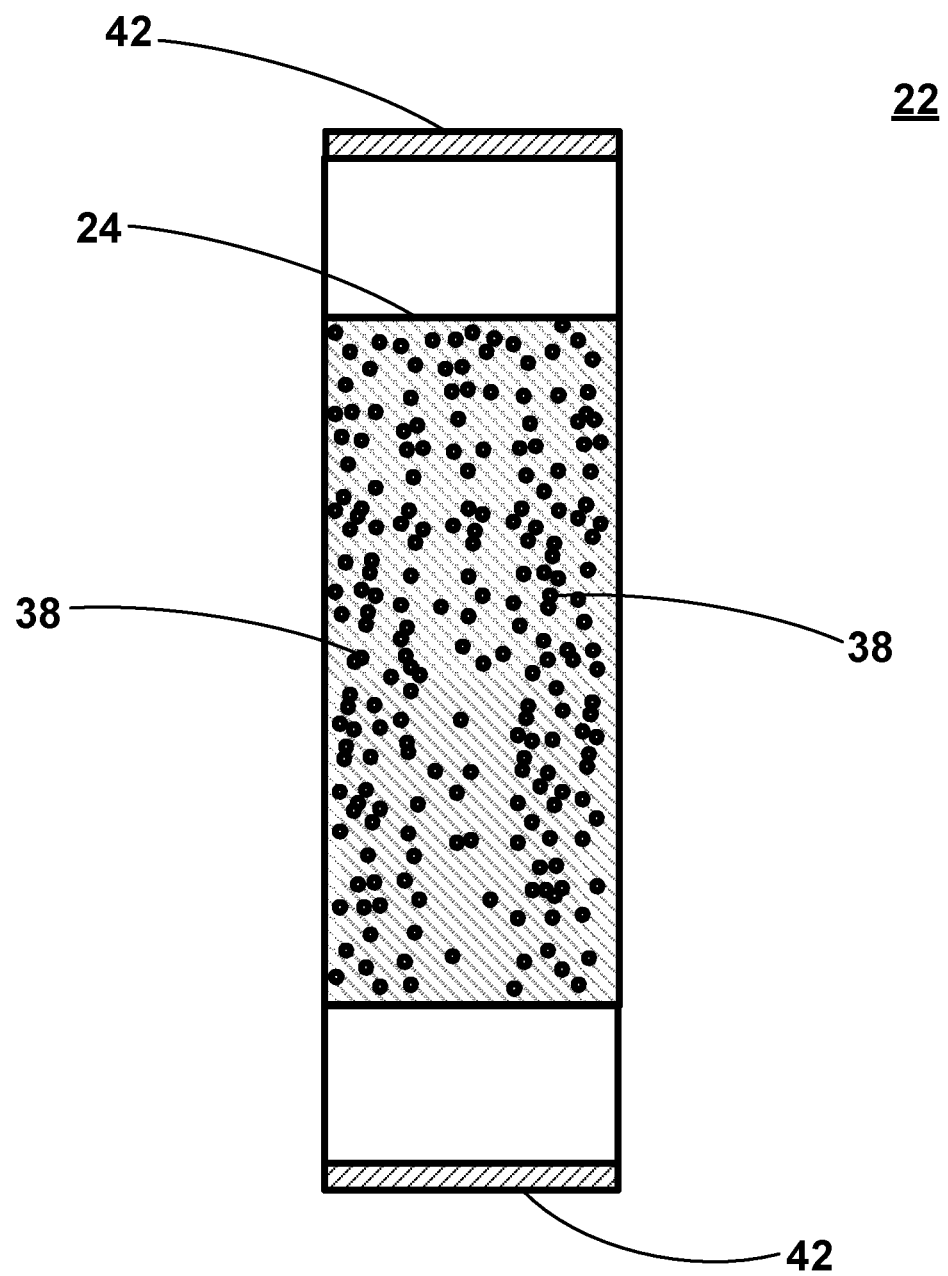
FIG. 4 is a cross-sectional side view illustration of a nicotine-bearing substrate located within a carrier unit configured for location within the vapour outlet conduit of the device or system according to one or more embodiments of the present invention.

FIG. 4 schematically illustrates a cross-sectional view of the carrier unit 22 in which is supported the substrate 24. The shape of carrier unit 22 may generally be dictated by the shape of the fluid passage 20 of the vapour outlet conduit 18, i.e. carrier unit 22 is shaped so as to fit in the fluid passage 20. Optionally, the carrier unit 22 may be cylindrical and the substrate 24 may be cylindrical to extend to the interior walls of the carrier unit 22.

Each end of the carrier unit 22 is sealed with a penetrable film 42. The penetrable film 42 is nicotine-impermeable so that the penetrable film 42 forms a nicotine-impermeable barrier to prevent nicotine and/or nicotine compounds escaping from the carrier unit 22 before use. The penetrable film 42 is penetrated during location of the carrier unit 22 in the vapour outlet conduit 18 to open a passage therein to atmosphere, i.e. to make the carrier unit 22 "ready-to-use".

Insertion of a carrier unit 22 into the vapour outlet conduit 18 of nicotine delivery device 11 will now be described with reference to FIGS. 5 and 6.

Figure 5:
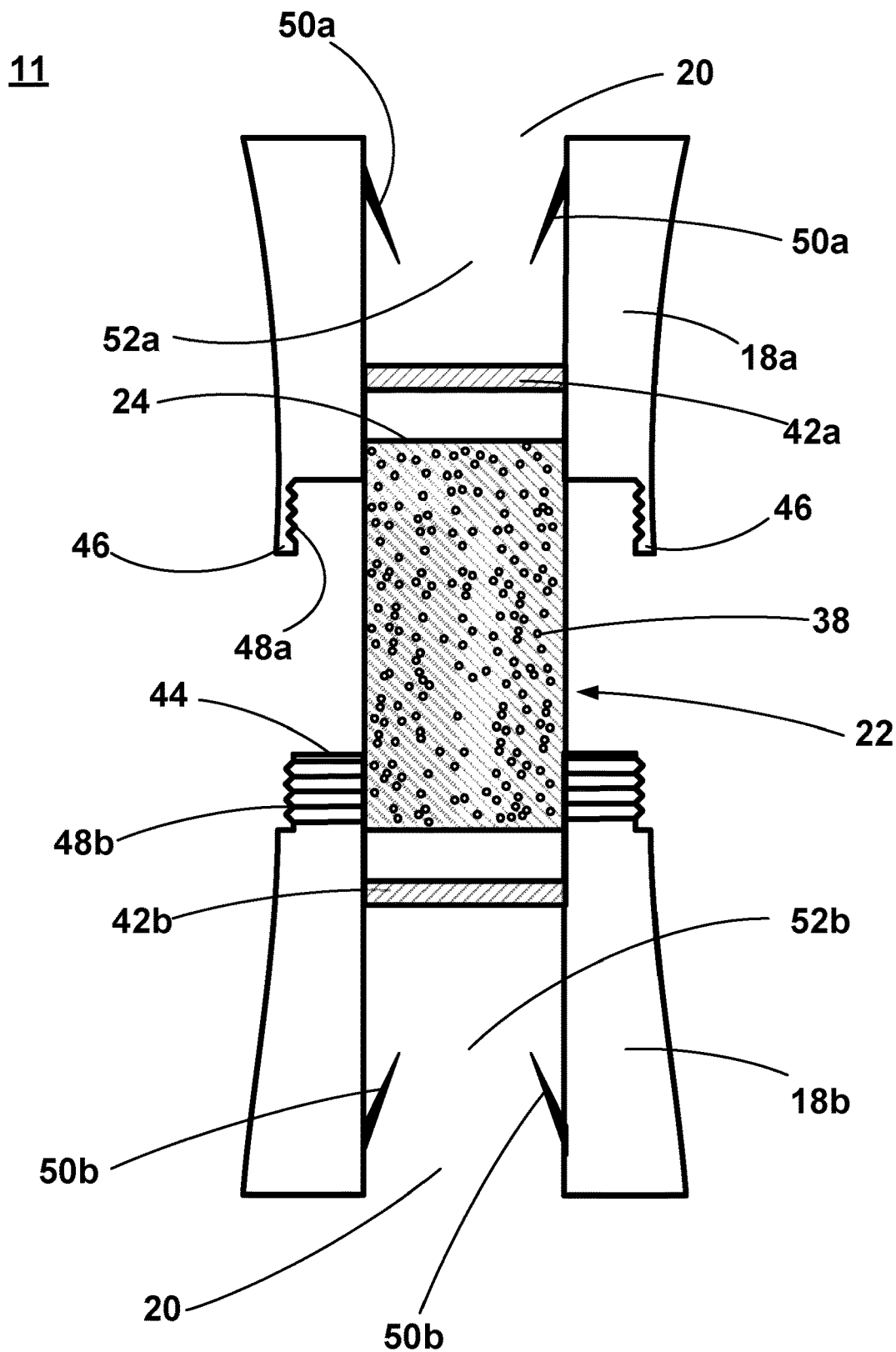
FIG. 5 is an exploded cross-sectional side view illustration of the vapour outlet conduit, carrier unit and nicotine-bearing substrate.

FIG. 5 is an exploded cross-sectional side view illustration of the vapour outlet conduit 18 and carrier unit 22. In this illustration, the vapour outlet conduit 18 is separated into a first part 18*a* and a second part 18*b*. Second part 18*b* has a reduced diameter section 44 for cooperating with overlap sections 46 on first part 18*a*. First part 18*a* is engageable to second part 18*b* by way of mutually cooperative interengagement formations located on said reduced diameter section 44 and overlap sections 46. In the illustrated arrangement, mutually cooperative interengagement formation located on said overlap sections 46 comprises screw thread 48*a* and mutually cooperative interengagement formation located on said reduced diameter section 44 comprises screw thread 48*b*. In optional arrangements, the first part 18*a* may be engageable to second part 18*b* by way of a push-fit arrangement, an interlocking arrangement, or by any other suitable mechanism for coupling first part 18*a* to second part 18*b*.

First part 18*a* and second part 18*b* are separable to permit removal of a carrier unit 22 from the vapour outlet conduit 18 (e.g. removal of a used carrier unit 22) and to allow a carrier unit 22 to be located in the vapour outlet conduit 18 (e.g. insertion of a replacement carrier unit 22).

In FIG. 5, the vapour outlet conduit 18 has been separated and a new carrier unit 22 has been inserted into the fluid passage 20. In order to complete the insertion process, the two parts 18*a* and 18*b* must be brought together to the state illustrated in FIG. 6. To achieve this from the state illustrated in FIG. 5, the user pushes the first part 18*a* and second part 18*b* together, so that the formations 48*a* move into initial engagement with the formations 48*b*. Continued movement of the first part 18*a* toward the second part 18*b* (or vice versa) moves the formations 48*a* and 486*b* through partial engagement, until the state illustrated in FIG. 6 is reached, i.e. the formations 48*a* and 48*b* are fully engaged.

As the two parts 18*a* and 18*b* are brought together about the carrier unit 22, prongs 50*a* in first part 18*a* approach penetrable film 42*a* at a first end of the carrier unit 22, and prongs 50*b* in second part 18*b* approach penetrable film 42*b* at a second end of the carrier unit. Bringing the two parts 18*a* and 18*b* closer together causes tips of the prongs 50*a* eventually to touch the penetrable film 42*a* and tips of prongs 50*b* eventually to touch the penetrable film 42*b*. Continued movement of the first part 18*a* toward the second part 18*b* (or vice versa) causes prongs 50*a* to penetrate penetrable film 42*a* and prongs 50*b* to penetrate penetrable film 42*b* (see FIG. 6, which shows the films 42*a* and 42*b* penetrated by prongs 50*a* and 50*b* respectively). A flap, or flaps (not shown) of penetrable film 42*a* and a flap, or flaps (not shown) of penetrable film 42*b* will be formed by the portion(s) of penetrable film 42*a*, 42*b* that is/are pushed aside as the prongs 50*a*, 50*b* penetrate the penetrable film to puncture a hole therethrough.

Prongs 50*a* define an aperture 52*a* therebetween through which air and/or vapour or aerosolised mist in the downstream region of fluid passage 20 can pass. Likewise, prongs 50*b* define an aperture 52*b* therebetween through which air and/or vapour or an aerosolised mist in the upstream region of fluid passage 20 can pass.

Figure 6:
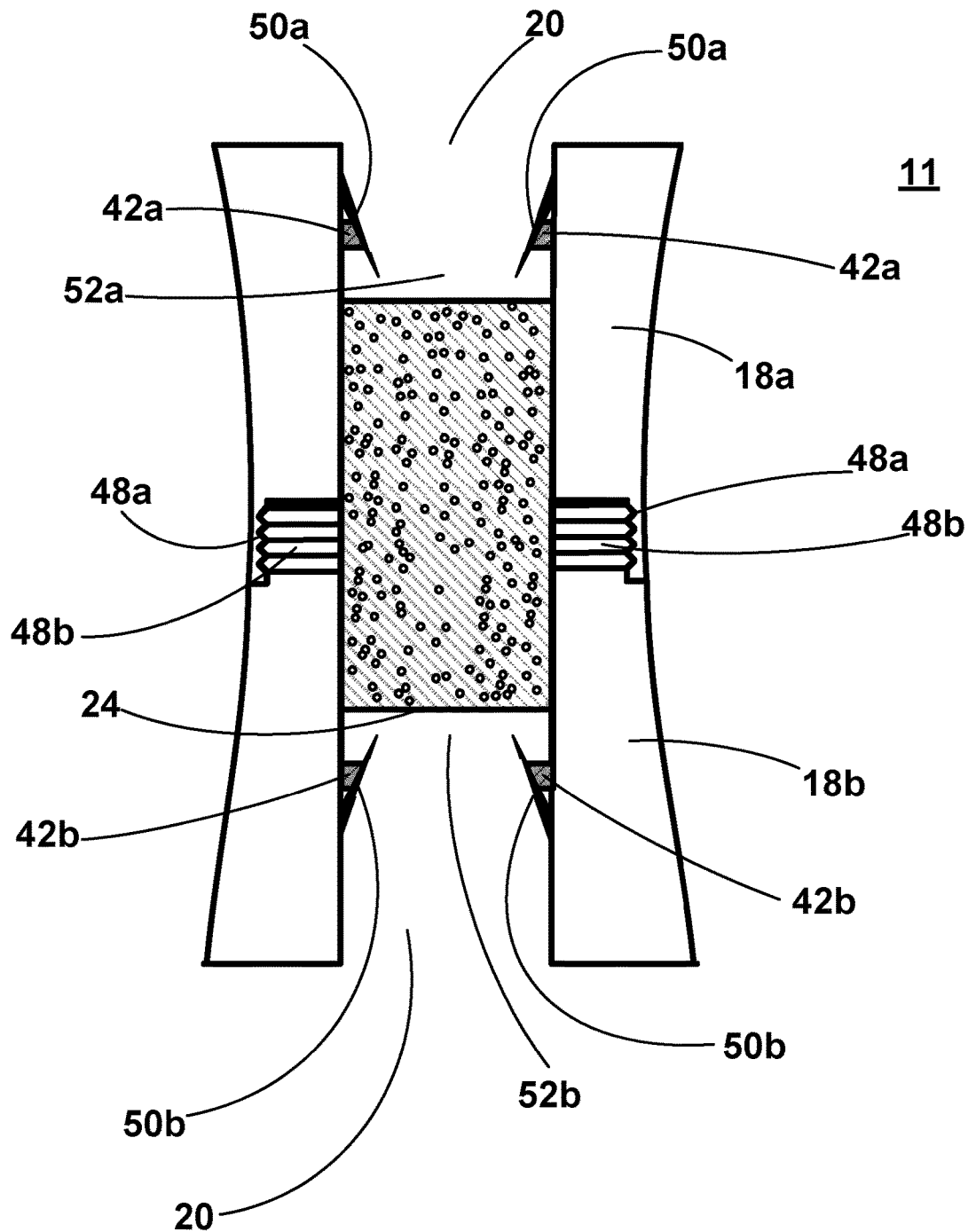
FIG. 6 is a cross-sectional side view illustration of the vapour outlet conduit, carrier unit and nicotine-bearing substrate.

With the carrier unit 22 located in the vapour outlet conduit 18 as shown in FIG. 6 (i.e. in the fluid passage 20 and with penetrable films 42*a* and 42*b* at both ends ruptured to create a fluid passage through the carrier unit 22), a user is able to suck on the vapour outlet conduit 18 and receive vapour or aerosolised mist for inhalation.

Figure 7:
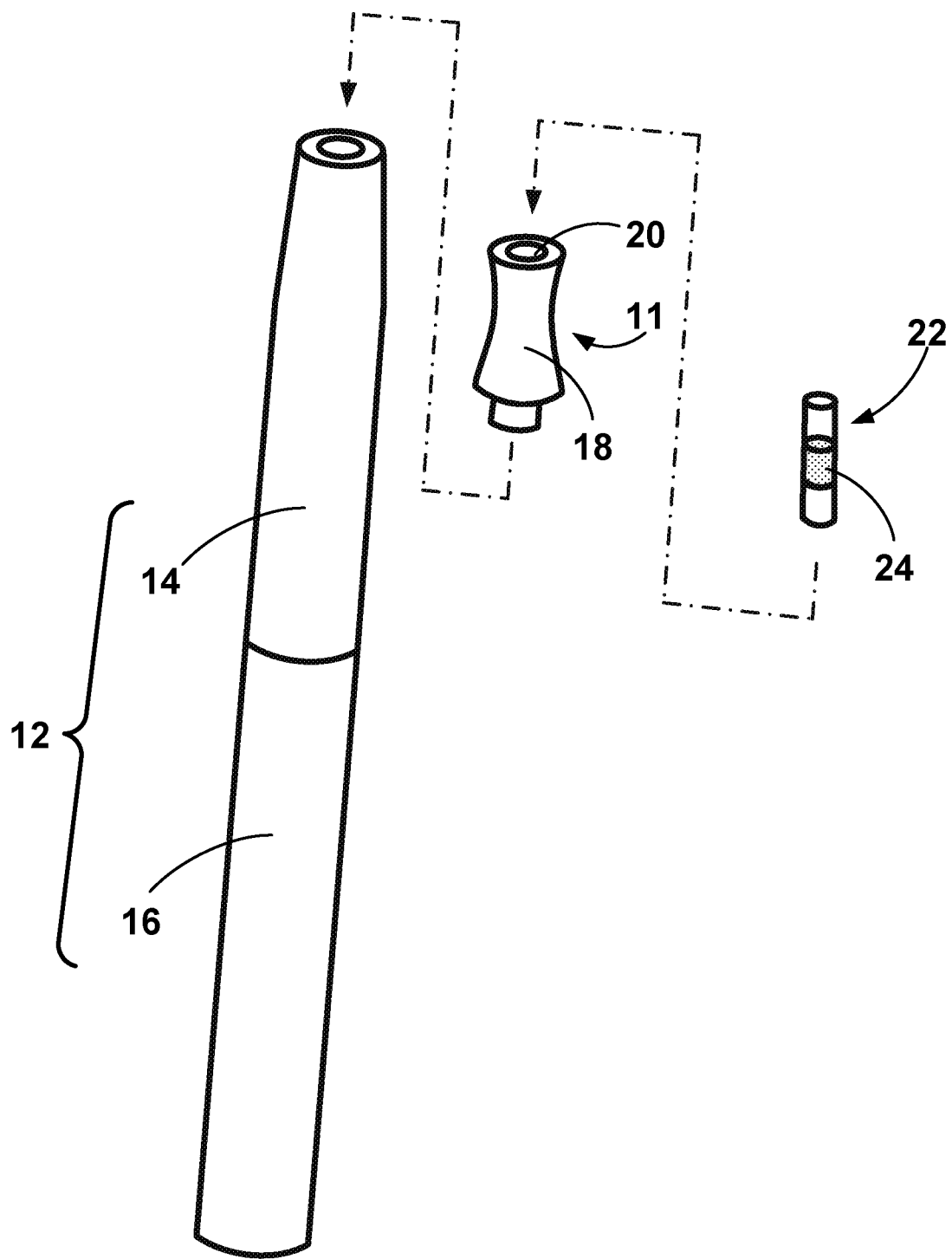
FIG. 7 is an exploded perspective view illustration of a kit-of-parts for assembling a system or device according to one or more embodiments of the present invention.

Optionally, nicotine delivery system 10 and/or nicotine delivery device 11 may be constructed from a kit-of-parts. FIG. 7 is an exploded perspective view illustration of a kit-of-parts for assembling a nicotine delivery system 10 or nicotine delivery device 11 according to one or more embodiments of the present invention.

Figure 8:
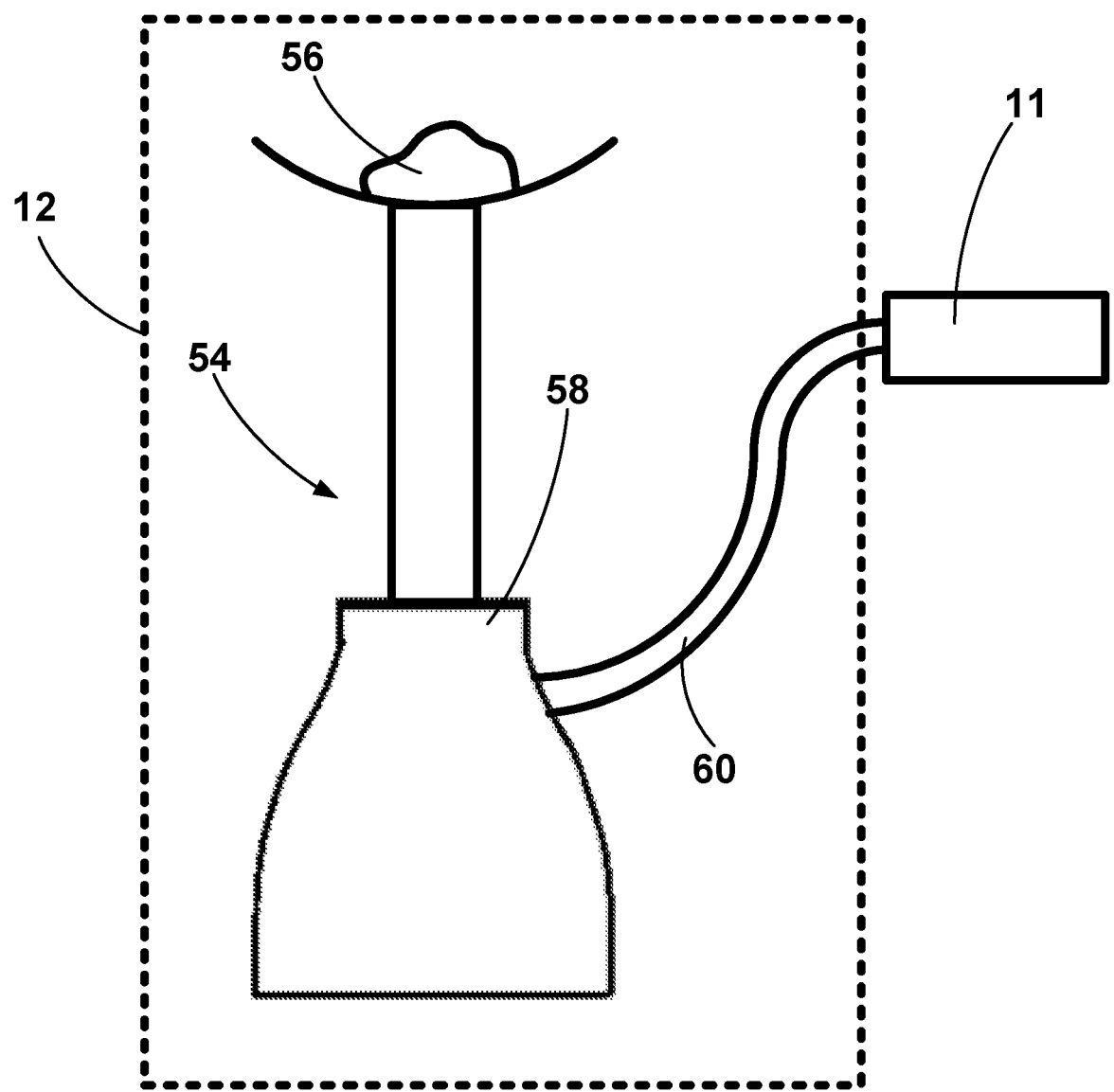
FIG. 8 is a schematic illustration of a system in an optional arrangement of one or more embodiments of the present invention.

FIG. 8 is a schematic illustration of a nicotine delivery system 10 in an optional arrangement of one or more embodiments of the present invention.

In this optional arrangement, the vapour creation system 12 comprises an apparatus 54 for creating an a vapour or aerosolised mist from ingredients for producing an aerosol mist or vapour 56 and in which the vapour or aerosolised mist is passed through a water basin 58 before inhalation. The nicotine delivery device 11 of the nicotine delivery system 10 is coupled to the water basin 58 by way of tube 60, which is in fluid communication with both the water basin 58 and nicotine delivery device 11. The apparatus 54 may comprise, for example, a so-called "hookah" (also known as waterpipe, narghile, arghila, or by other names).

There has been described in the foregoing one or more embodiments of a nicotine delivery device and nicotine delivery system that avoids or at least ameliorates the problems of the prior art.

As used herein any reference to "one embodiment" or "an embodiment" means that a particular element, feature, structure, or characteristic described in connection with the embodiment is included in at least one embodiment. Any appearances of the phrase "in one embodiment" or the phrase "in an embodiment" in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

In view of the foregoing description it will be evident to a person skilled in the art that various modifications may be made within the scope of the invention. For example, although a battery and vaporizer combination, or a "hookah" apparatus have been described in the foregoing as examples of vapour or aerosolized mist creation systems 12, embodiments in accordance with the present invention are not limited to using such items. Although one or more embodiments have been described with reference to nicotine precursors, or nicotine, or nicotine containing substrates or compounds, nicotine may be substituted with or supplemented with a further ingredient, for example a pain relief compound, flavouring or other substance suitable for inhalation via a vapour or aerosolized mist.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. A device for delivery of a substance, wherein the substance comprises at least one of nicotine and a flavouring, the device comprising:
a vapour outlet conduit for coupling to, and for fluid communication with, a vapour creation system, said vapour outlet conduit defining a fluid passage therethrough for delivery of vapour from a vapour creation system to a user;
wherein said vapour outlet conduit comprises a substance carrier unit region configured to accept a substance carrier unit and retain said substance carrier unit in said fluid passage,
wherein the vapour outlet conduit comprises penetrating elements for penetrating penetrable seals of the substance carrier unit, such that when the substance carrier unit is located in the fluid passage, the penetrating elements provide a first aperture through which air and/or vapour in a downstream region of the vapour passage can pass and the penetrating elements provide a second aperture through which air and/or vapour in an upstream region of the vapour passage can pass.

2. A device according to claim 1, wherein said vapour outlet conduit is releasably coupleable to said vapour creation system to permit location of said substance carrier unit in said vapour outlet conduit.

3. A device according to claim 1, wherein said vapour outlet conduit is separable to permit location of said substance carrier unit therein.

4. A device according to claim 1, further comprising a substance carrier unit located in said fluid passage, said substance carrier unit configured for removable location within said fluid passage and comprising a substance-bearing substrate configured for entraining the substance in a vapour stream received from said vapour creation system as said vapour stream passes through said vapour outlet conduit.

5. A device according to claim 4, wherein said substance carrier unit is configured, and located within said vapour outlet conduit, for passage of said vapour stream over said substance-bearing substrate.

6. A device according to claim 4, wherein said substance carrier unit is configured, and located within said vapour outlet conduit, for passage of said vapour stream through said substance-bearing substrate.

7. A device according to claim 4, wherein said substance-bearing substrate comprises a porous material where pores of said porous material contain at least one of: nicotine, a nicotine precursor; and a nicotine compound.

8. A device according to claim 7, wherein said porous material comprises a sintered material.

9. A device according to claim 4, wherein said substance-bearing substrate comprises polypropylene or polyethylene terephthalate.

10. A device according to claim 4, wherein said substance carrier unit further comprises a housing for housing said substance-bearing substrate.

11. A device according to claim 10, wherein said housing defines a passageway in which is located the substance-bearing substrate.

12. A device according to claim 10, wherein said housing comprises the penetrable seals for closing open ends of said passageway, said penetrable seals penetrable to permit fluid communication through said passageway.

13. A device according to claim 1, wherein said vapour outlet conduit comprises a mouthpiece of said substance delivery device.

14. A substance carrier unit for a device according claim 1, wherein said substance carrier unit is configured for removable location within said fluid passage and comprising a substance-bearing substrate configured for releasing a substance to a vapour stream as said vapour stream passes through said vapour outlet conduit, wherein the substance comprises at least one of nicotine and a flavouring, wherein the substance carrier unit comprises a first penetrable seal at a first end of the substance carrier unit and a second penetrable seal at a second end of the substance carrier unit, such that when the substance carrier unit is located within the fluid passage, penetrating elements of the vapour outlet conduit penetrate the penetrable seals, such that the penetrating elements provide a first aperture through which air and/or vapour in a downstream region of the vapour passage can pass and the penetrating elements provide a second aperture through which air and/or vapour in an upstream region of the vapour passage can pass.

15. A system delivery of a substance, wherein the substance is at least one of nicotine and a flavouring, comprising:
   a delivery device according to claim 1; and
   a vapour creation system coupled to said vapour outlet conduit of said delivery device.

16. A kit-of-parts for assembling a device for delivery of a substance, wherein the substance comprises at least one of nicotine and a flavouring, the kit-of-parts comprising:
   a vapour outlet conduit configured for coupling to, and for fluid communication with, a vapour creation system, said vapour outlet conduit defining a vapour passage therethrough for delivery of vapour from a vapour creation system to a user, wherein said vapour outlet conduit comprises a substance carrier unit region configured to accept a substance carrier unit and retain said substance carrier unit in said fluid passage, wherein the vapour outlet conduit comprises penetrating elements for penetrating penetrable seals of the substance carrier unit; and
   a substance carrier unit configured for removable location in said fluid passage, said substance carrier unit comprising a substance-bearing substrate configured for releasing the substance to a vapour stream as said vapour stream passes through said vapour outlet conduit, wherein the substance carrier unit comprises a first penetrable seal at a first end of the substance carrier unit and a second penetrable seal at a second end of the substance carrier unit, such that when the substance carrier unit is located within the fluid passage, the penetrating elements of the vapour outlet conduit penetrate the penetrable seals, such that the penetrating elements provide a first aperture through which air and/or vapour in a downstream region of the vapour passage can pass and the penetrating elements provide a second aperture through which air and/or vapour in an upstream region of the vapour passage can pass.

17. A kit-of-parts for assembling a system for delivery of a substance, wherein the substance comprises at least one of nicotine and a flavouring, the kit-of-parts comprising:
   a vapour outlet conduit configured for coupling to, and for fluid communication with, a vapour creation system, said vapour outlet conduit defining a vapour passage therethrough for delivery of vapour from a vapour creation system to a user, wherein said vapour outlet conduit comprises a substance carrier unit region configured to accept a substance carrier unit and retain said substance carrier unit in said fluid passage, wherein the vapour outlet conduit comprises penetrating elements for penetrating penetrable seals of the substance carrier unit;
   a substance carrier unit configured for removable location in said fluid passage, said substance carrier unit comprising a substance-bearing substrate configured for releasing the substance to a vapour stream as said vapour stream passes through said vapour outlet conduit, wherein the substance carrier unit comprises a first penetrable seal at a first end of the substance carrier unit and a second penetrable seal at a second end of the substance carrier unit, such that when the substance carrier unit is located within the fluid passage, the penetrating elements of the vapour outlet conduit penetrate the penetrable seals, such that the penetrating elements provide a first aperture through which air and/or vapour in a downstream region of the vapour passage can pass and the penetrating elements provide a second aperture through which air and/or vapour in an upstream region of the vapour passage can pass; and
   a vapour creation system for coupling to said vapour outlet conduit.

* * * * *